United States Patent
Schuman, Jr.

(10) Patent No.: US 9,078,964 B2
(45) Date of Patent: Jul. 14, 2015

(54) PUMP DEVICE, TUBE DEVICE AND METHOD FOR MOVEMENT AND COLLECTION OF FLUID

(75) Inventor: Peter J. Schuman, Jr., West Sand Lake, NY (US)

(73) Assignee: SUR-Real Industries, Inc., West Sand Lake, NY (US)

( * ) Notice: Subject to any disclaimer, the term of this patent is extended or adjusted under 35 U.S.C. 154(b) by 0 days.

(21) Appl. No.: 12/534,903

(22) Filed: Aug. 4, 2009

(65) Prior Publication Data

US 2010/0049134 A1    Feb. 25, 2010

Related U.S. Application Data

(60) Provisional application No. 61/090,730, filed on Aug. 21, 2008.

(51) Int. Cl.

| | |
|---|---|
| *F04B 43/08* | (2006.01) |
| *A61M 1/00* | (2006.01) |
| *A61M 5/142* | (2006.01) |
| *A61M 1/10* | (2006.01) |
| *F04B 43/00* | (2006.01) |
| *F04B 43/12* | (2006.01) |
| *A61M 39/10* | (2006.01) |

(52) U.S. Cl.
CPC .......... *A61M 5/14228* (2013.01); *A61M 1/1039* (2014.02); *A61M 39/10* (2013.01); *F04B 43/0072* (2013.01); *F04B 43/12* (2013.01); *A61M 1/0066* (2013.01); *A61M 5/14212* (2013.01); *A61M 2039/1022* (2013.01)

(58) Field of Classification Search
CPC .......... A61M 1/0066; A61M 5/14228; A61M 1/1037; A61M 1/1039; A61M 5/14212; A61M 39/10; A61M 2039/1022; A61M 2039/265; A61M 2205/6027; F04B 43/12; F04B 43/0072; F04B 43/0054; F04B 43/08; F04B 43/09
USPC ............ 604/29, 151–153, 30–31, 6.11, 6.12, 604/35; 417/474, 53, 476–477.2, 412
See application file for complete search history.

(56) References Cited

U.S. PATENT DOCUMENTS

| | | |
|---|---|---|
| 3,908,657 A | 9/1975 | Kowarski |
| 3,993,079 A | 11/1976 | Henriques de Gatztanondo |
| 4,029,099 A | 6/1977 | Fifield |
| 4,236,880 A * | 12/1980 | Archibald ..................... 417/478 |

(Continued)

FOREIGN PATENT DOCUMENTS

| | | |
|---|---|---|
| JP | 63-154182 | 6/1988 |
| JP | 2002538899 | 11/2002 |

(Continued)

OTHER PUBLICATIONS

GI Supply, "The Rp Paracentesis System", Date Unknown, pp. 1-2.

(Continued)

*Primary Examiner* — Bhisma Mehta
*Assistant Examiner* — Jenna Zhang
(74) *Attorney, Agent, or Firm* — Woodard, Emhardt, Moriarty, McNett & Henry LLP

(57) ABSTRACT

A pump device, tube device and method for the aspiration, peristaltic movement and collection of fluid. A rigid tube for drawing fluid connected to a primary flexible tube. The primary flexible tube inserted through a peristaltic pump.

23 Claims, 5 Drawing Sheets

(56) References Cited

U.S. PATENT DOCUMENTS

| | | | |
|---|---|---|---|
| 4,392,858 A | | 7/1983 | George et al. |
| 4,447,235 A | | 5/1984 | Clarke |
| 4,661,093 A | | 4/1987 | Beck et al. |
| 4,755,168 A | | 7/1988 | Romanelli et al. |
| 4,784,156 A | | 11/1988 | Garg |
| 4,820,265 A | * | 4/1989 | DeSatnick et al. ............... 604/30 |
| 4,963,131 A | * | 10/1990 | Wortrich .......................... 604/34 |
| 4,966,580 A | | 10/1990 | Turner et al. |
| 5,125,891 A | | 6/1992 | Hossain et al. |
| 5,213,483 A | * | 5/1993 | Flaherty et al. ............. 417/477.2 |
| 5,259,843 A | | 11/1993 | Watanabe et al. |
| 5,282,787 A | | 2/1994 | Wortrich |
| 5,322,422 A | * | 6/1994 | Natwick et al. ............... 417/474 |
| 5,697,898 A | | 12/1997 | Devine |
| 5,911,222 A | | 6/1999 | Lawrence et al. |
| 5,927,951 A | * | 7/1999 | Tamari ............................ 417/63 |
| 5,928,257 A | | 7/1999 | Kablik et al. |
| D420,738 S | | 2/2000 | Carter et al. |
| 6,319,223 B1 | | 11/2001 | Wortrich et al. |
| 6,494,693 B1 | * | 12/2002 | Sunden ....................... 417/477.7 |
| 7,168,930 B2 | * | 1/2007 | Cull et al. .................. 417/477.8 |
| 7,186,230 B2 | | 3/2007 | Briggs et al. |
| 7,198,751 B2 | * | 4/2007 | Carpenter et al. .............. 422/45 |
| 7,273,359 B2 | * | 9/2007 | Blight et al. ............. 417/477.13 |
| 7,291,128 B2 | | 11/2007 | Rossi et al. |
| 7,922,148 B2 | * | 4/2011 | Walborn ....................... 251/128 |
| 8,052,642 B2 | | 11/2011 | Harr et al. |
| 8,052,643 B2 | | 11/2011 | Hudson et al. |
| 8,053,721 B2 | | 11/2011 | Bisch et al. |
| 8,142,399 B2 | | 3/2012 | Hanlon et al. |
| 8,142,404 B2 | | 3/2012 | Knauper et al. |
| 8,154,274 B2 | | 4/2012 | Wiesner |
| 2004/0049157 A1 | | 3/2004 | Plishka et al. |
| 2004/0127840 A1 | * | 7/2004 | Gara et al. ................... 604/4.01 |
| 2005/0069437 A1 | * | 3/2005 | Mittelstein et al. ........ 417/477.2 |
| 2005/0118048 A1 | * | 6/2005 | Traxinger ................. 417/477.2 |
| 2007/0282268 A1 | | 12/2007 | Mayse |

FOREIGN PATENT DOCUMENTS

| | | |
|---|---|---|
| JP | 2005-103257 | 4/2005 |
| JP | 2007-236597 | 9/2007 |
| WO | WO 00/54824 | 9/2000 |

OTHER PUBLICATIONS

Lexis-Nexis Total Patent English Translation of JP 2007-236597, Entitled: Transfusion Apparatus, Published Sep. 20, 2007, Applicant: Atom Medical Corp. English Translation obtained Apr. 2, 2014.

NPL—Patent Abstracts of Japan, English Translation of Abstract, JP 2007-236597, Entitled, Transfusion Apparatus, Published Sep. 20, 2007, Applicant: Atom Medical Corp.

* cited by examiner

PUMP DEVICE, TUBE DEVICE AND METHOD FOR MOVEMENT AND COLLECTION OF FLUID

FIELD OF THE INVENTION

The present invention relates generally to the movement of fluid, and more specifically relates to a pump device, tube device and method for the peristaltic movement and collection of fluid.

BACKGROUND OF THE INVENTION

The movement of fluid from a body of fluid to another point for collection is a routine need and can be performed in a number of ways. When tubing or piping is used for carrying the fluid during the movement either gravity or a pump is needed to either create and/or sustain the suction needed to move the fluid from one point to another.

At times the movement of fluid from the body of fluid must be performed in a gentle, slow and steady manner. This gentle, slow and steady manner is also known as peristalsis. Peristaltic pumping may be performed in a number of ways including, but not exclusively, by hand pump or with the use of a peristaltic pump.

In medical care, thoracentesis and paracentesis is typically performed by hand pumping, to achieve the peristaltic movement of excess fluid in a patient's body into drainage bags for disposal or syringes for laboratory analysis or any other medical use. Hand pumping is time consuming and requires a person to be in attendance at all times. Further, the attendant must manually perform the hand pumping necessary to sustain the peristaltic movement. It is difficult to generate consistent suction forces using hand pumping. Depending upon the amount of excess fluid, hand pumping may take several hours of manual labor.

Additional known methods for thoracentesis and paracentesis include glass vacuum suction bottles and wall/portable suction. These methods typically produce a constant suction rather than a peristaltic suction. Glass vacuum bottles often break in shipping causing inadequate suction; are bulky and fragile causing storage, operational and shipping difficulties; typically are limited in size necessitating frequent changes during the procedure; require special medical waste handling procedures; and when shattered in use create the danger of shattered glass and the contamination problem of body fluids. Wall suction, in addition to providing only constant suction, is not readily available in all clinical settings. Wall units are expensive to retrofit in existing facilities. Portable units may cost thousands of dollars. Both wall and portable units typically have small capacities requiring frequent changes during the course of a procedure. Wall units tend to create greater suction forces than is safe for thoracentesis and paracentesis.

SUMMARY OF THE INVENTION

A pump device, tube device and method for the peristaltic movement and collection of fluid.

A first aspect of the invention provides a pump device for the peristaltic movement of fluid comprising: a rigid tube; a primary flexible tube, wherein the primary flexible tube is connected to the rigid tube; and a peristaltic pump, wherein the primary flexible tube is inserted through the peristaltic pump.

A second aspect of the invention provides a tube device for the peristaltic movement and collection of fluid comprising: an aspirator; a rigid tube; a primary flexible tube, wherein the primary flexible tube is configured for insertion through a peristaltic pump; and a collection receptacle.

A third aspect of the invention provides a method of utilizing a peristaltic pump, tubing and receptacle for the peristaltic movement and collection of fluid comprising: drawing a fluid from a collection of fluid with an aspirator; moving the fluid away from the collection of fluid with a rigid tube; moving the fluid away from the rigid tube with a primary flexible tube; pumping the fluid in a peristaltic manner by inserting the primary flexible tube through a peristaltic pump; and receiving the fluid in a collection receptacle.

BRIEF DESCRIPTION OF THE DRAWINGS

These and other features of this invention will be more readily understood from the following detailed description of the various aspects of the invention taken in conjunction with the accompanying drawings in which.

DETAILED DESCRIPTION OF THE INVENTION

Figure 1:
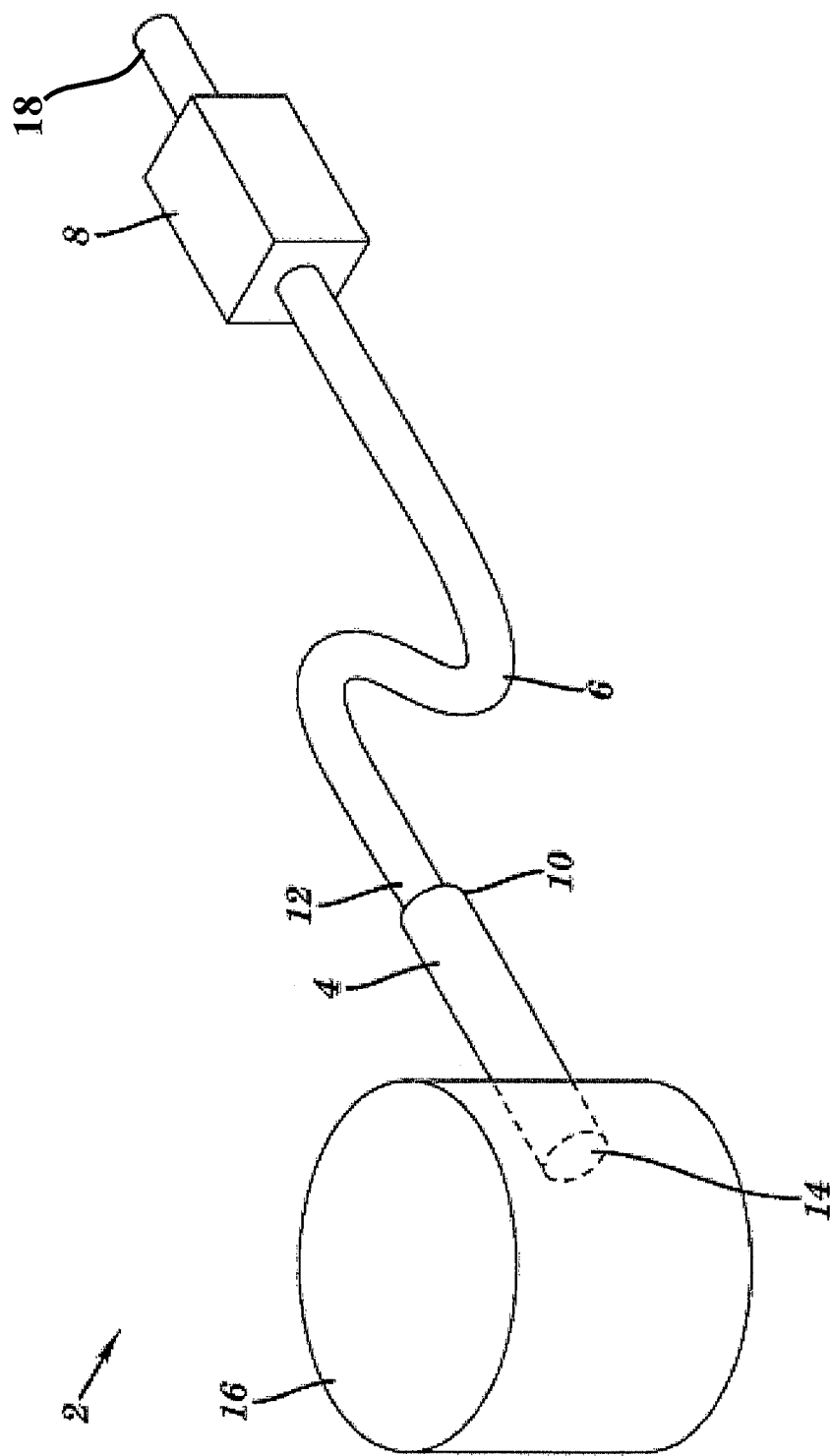
FIG. 1 shows one embodiment of the pump device.

As seen in FIG. 1, one embodiment of the pump device 2 is shown comprised of a rigid tube 4, a primary flexible tube 6, and a peristaltic pump 8. A first end of the rigid tube 10 is connected to a first end of the primary flexible tube 12. The primary flexible tube 6 is inserted through the peristaltic pump 8.

To operate the pump device 2, a second end of the rigid tube 14 is inserted in a collection of fluid 16 and the fluid is drawn through the rigid tube 4 and the primary flexible tube 6 and discharged at a second end of the primary flexible tube 18.

The peristaltic pump 8 may be any available peristaltic pump 8 that permits the application of peristaltic motion to the primary flexible tube 6. In one embodiment the peristaltic pump 8 is electrically powered. Further, in one embodiment the rate of the peristaltic pump 8 can be adjusted. One example of a peristaltic pump 8 as described herein is the Renal Systems Minipump® RS-7800™ by Renal Systems, Inc. In one embodiment, the peristaltic pump 8 is placed below the level of the collection of fluid 16 to improve fluid extraction. The collection of fluid 16 could be in a living being (not shown).

Figure 2:
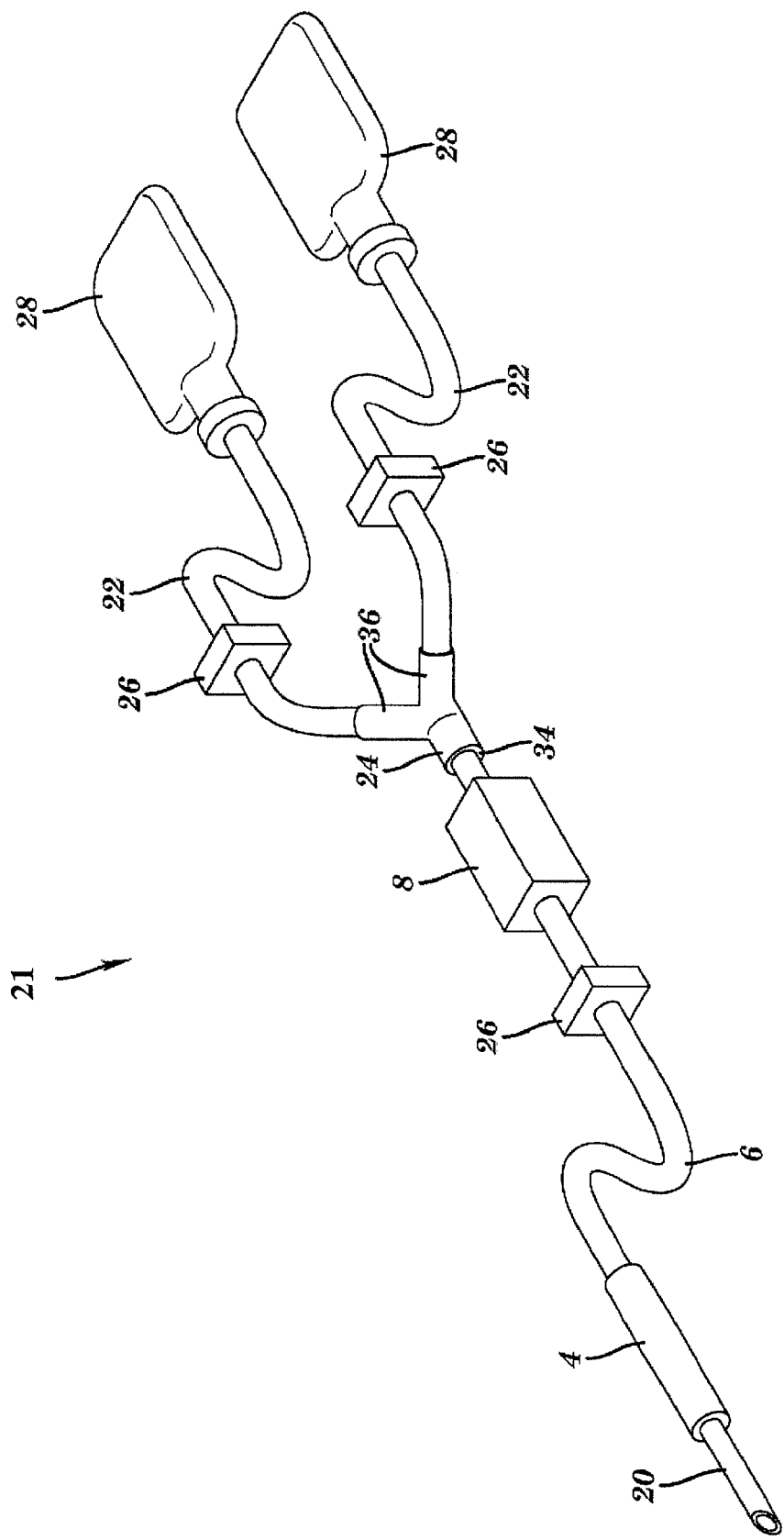
FIG. 2 shows one embodiment of the tube device.

As seen in FIG. 2, one embodiment of the tube device 21 is shown comprised of an aspirator 20, the rigid tube 4, the primary flexible tube 6, a plurality of secondary flexible tubes 22, a connector 24, a plurality of at least one of clamps or valves 26, and a plurality of collection receptacles 28. The aspirator 20 may be a sheath needle, a catheter or any number of aspiration devices. The plurality of collection receptacles 28 could include at least one of drainage bags 30 and syringes 32 (see FIG. 4). A person skilled in the art will recognize many arrangements of the rigid tube 4, the primary flexible tube 6, the plurality of secondary flexible tubes 22, the connector 24, the plurality of at least one of clamps or valves 26 and the syringe 32, where a syringe 32 could be placed between the collection of fluid 16 and collection bag 30 in order to facilitate removal of fluid using the syringe 32.

One embodiment of the connector 24 provides one inflow 34 and two outflows 36 but the invention could have a connector 24 that provides any number of outflows.

One embodiment of the plurality of clamps and valves 26 is illustrated but the invention can utilize any combination of clamps and valves 26 depending upon the user's needs. In one embodiment of the invention, at least one of the valves 26 could be a one way valve placed on either the rigid tube 4 or primary flexible tube 6 between the collection of fluid 16 and peristaltic pump 8 to restrict the flow of fluid to one direction.

The aspirator 20 is illustrated as a sheath needle but the invention can utilize any number of aspirators including but not limited to a catheter.

The rigid tube 4, the primary flexible tube 6, and secondary flexible tubes 22 are not restricted to a specific length or cross-section. A person skilled in the art will readily recognize that the rigid tube 4, the primary flexible tube 6, and the secondary flexible tubes 22 could be fused into one continuous length of tubing of that varied over its length with respect to outer diameter, inner diameter, wall strength, and degree of rigidity/flexibility.

The plurality of collection receptacles 28 may be any combination of receptacles required by the user. The collection receptacles 28 may be any volume required by the user.

Figure 3:
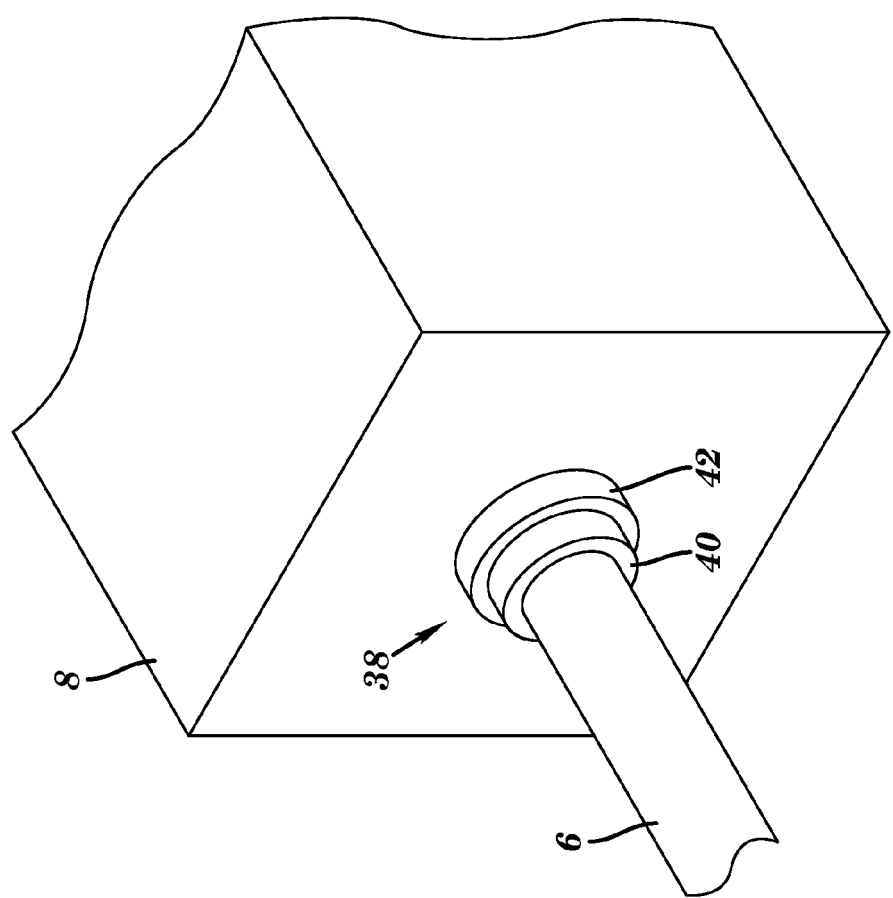
FIG. 3 shows one embodiment of a partial view of the tube or pump device.

As seen in FIG. 3, one embodiment of a partial view of the invention is shown. A circuit connection 38 is provided wherein the electric circuit for the peristaltic pump 8 is complete when the primary flexible tube 6 is inserted through the peristaltic pump 8. A person skilled in the art will readily recognize that many devices for a circuit connection 38 could be used. In one embodiment, the circuit connection 38 is comprised of a flexible tube connection 40 (e.g., a first connector) and a pump connection 42 (e.g., a second connector). When the primary flexible tube 6 is inserted through the peristaltic pump 8 the flexible tube connection 40 and the pump connection 42 come into contact with each other. Coming into contact with each other completes the circuit connection 38 turning the peristaltic pump 8 power on. The flexible tube connection 40 and the pump connection 42 may be made of any known circuit connector devices and materials. In one embodiment, the two connections are comprised of magnets.

Figure 4:
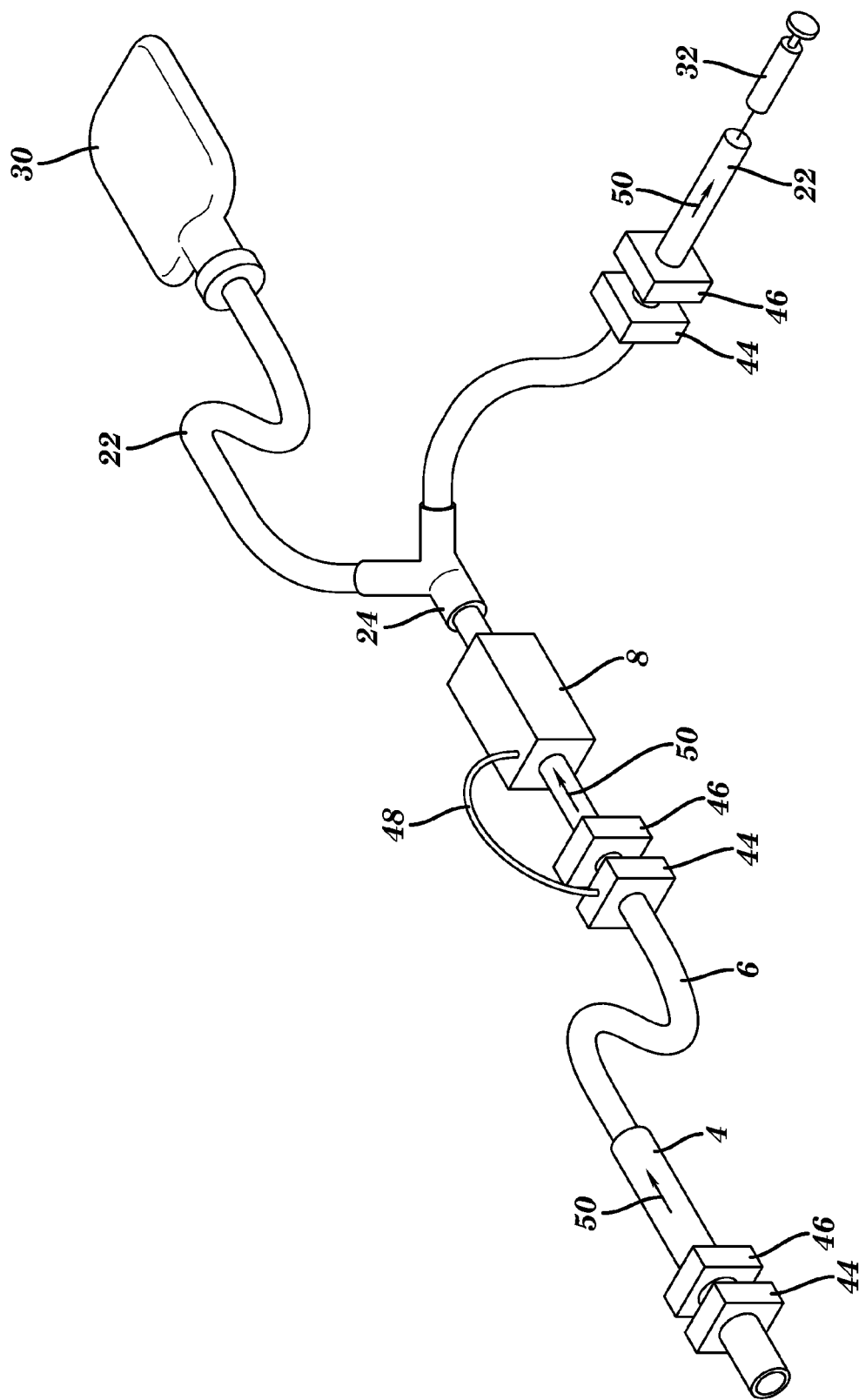
FIG. 4 shows one embodiment of the tube device.

As seen in FIG. 4, one embodiment of the tube device 12 is shown. A plurality of fluid movement sensors 44 is provided. The fluid movement sensors 44 may be attached to any point along the rigid tube 4, primary flexible tube 6, or secondary flexible tubes 22. The fluid movement sensors 44 may detect whether fluid is moving or measure the amount of fluid moving. The amount of fluid moving could be measured by rate, volume, or any other flow measurement. The fluid movement sensor 44 may be connected to an alarm 46. The alarm 46 may have an audible, visual, or vibratory signal or any other type of signal. The fluid movement sensor 44 may be connected by connection 48 to the peristaltic pump 8 to regulate the flow of the movement either by adjusting the flow volume or stopping the flow completely.

The invention may include a plurality of directional arrows 50 on the rigid tube 4, the primary flexible tube 6, the secondary flexible tubes 22, the peristaltic pump 8, the aspirator 20, the clamps and valves 26, or the collection receptacles 28. The directional arrows 50 may be utilized to inform a user of fluid movement direction or to provide installation instructions to a user.

Figure 5:
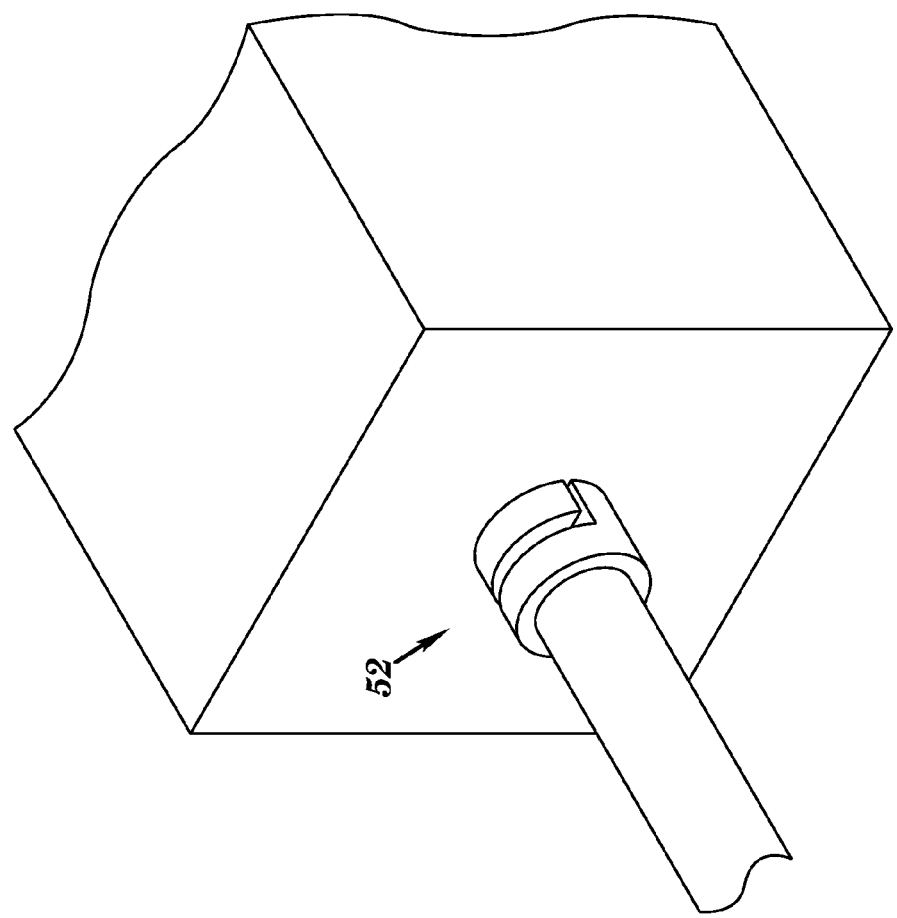
FIG. 5 shows one embodiment of a partial view of the tube or pump device.

As seen in FIG. 5, one embodiment of a partial view of the tube or pump device is shown. A directional coupling mechanism 52 is provided that restricts the inserting of the primary flexible tube 6 through the peristaltic pump 8 to a specific direction.

In one embodiment, the invention is used for thoracentesis and paracentesis. The collection of fluid 16 is the excess fluid that can accumulate in a living being due to any number of causes. The aspirator 20 could be a sheath needle or a catheter inserted in the living being using standard techniques. The rigid tube 4 permits movement away from the living being and resisting collapse of the rigid tube 4 as the fluid is moved from the living being. The primary flexible tube 6 is inserted through the peristaltic pump 8. A connector 18 with clamps and/or valves 26 permits the collection of excess fluid. The collection receptacles 28 could be one or more drainage bags 30 or syringes 32. When one collection receptacle 28 is filled, the use of clamps or valves 26 permits redirection of the fluid to another collection receptacle 28. A syringe 32 or other device may be used to collect samples of the excess fluid.

The method of peristaltic movement and collection of fluid will be readily understood by the description of the pump device 2 and tube device 12. The peristaltic pump 8 provides the means for a gentle draw of the fluid. The rigid tube 4, primary flexible tube 6, and secondary flexible tubes 16 provide the means for the fluid to move effectively and properly. The clamps and valves 26 allow the user to control the flow of the fluid. A connector 24 with one inflow 34 and a plurality of outflows 36 allows the user to adapt the method for various types of fluid movement purposes. The collection receptacles 28 provide a place for the discharge of the fluid. While the embodiment of the method generally utilizes collection receptacles 28 for fluid discharge, it should be readily understood that discharge of the fluid could occur without collection receptacles.

In one embodiment, the device and method is used for thoracentesis or paracentesis. It is uniquely useful for large volumes of excess fluid (>250 ml). The peristaltic pump 8 does not produce continuous high suction forces. The peristaltic pump 8 draws fluid with gentle intermittent pulsations.

Advantages in the medical field include greater safety to the patient. The invention balances the gentle draw fluid with a rate of fluid removal equal to or higher to methods now in use. The invention eliminates the need for hand pumping. The invention eliminates the need for a wall section device to be present in the procedure room. The invention eliminates the need for glass vacuum bottles thereby reducing hazards, greater expense, and difficult storage issues. The elimination of changing glass vacuum bottles also greatly diminishes the risks of needle stick and fluid splash.

The aspirator 20 could be a sheath needle or catheter system allowing fluid to be accessed within the abdomen or chest cavity of a living being. The YUEH Centesis Disposable Catheter Needle™ by Cook Urological, Inc. has been used successfully but one skilled in the art will understand that any number of fluid access and drainage devices may be used.

The primary flexible tube 6 and/or secondary flexible tubes 22 could be made of 20" Male to Female High Pressure Injector Tubing which has been used successfully but one skilled in the art will understand that various types of tubing may be used for the primary flexible tube 6 and/or secondary flexible tubes 22. The primary flexible tube 6 and/or secondary flexible tubes 22 allow for efficient fluid flow between the aspirator 20 and the collection receptacles 28. The primary flexible tube 6 and/or secondary flexible tubes 22 provide necessary length to the invention to allow the peristaltic pump 8 to rest conveniently and safely on the floor below and away from the living being.

As used herein, an element or step recited in the singular and proceeded with the word "a" or "an" should be understood as not excluding plural elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

While various embodiments are described herein, it will be appreciated from the specification that various combinations of elements, variations or improvements therein may be made by those skilled in the art, and are within the scope of the invention. In addition, many modifications may be made to adapt a particular situation or material to the teachings of the invention without departing from essential scope thereof. Therefore, it is intended that the invention not be limited to the particular embodiment disclosed as the best mode contemplated for carrying out this invention, but that the invention will include all embodiments falling within the scope of the appended claims.

The foregoing description of the invention has been presented for purposes of illustration and description. It is not intended to be exhaustive or to limit the invention to the precise form disclosed, and obviously, many modifications and variations are possible. Such modifications and variations that may be apparent to a person skilled in the art are intended to be included within the scope of this invention as defined by the accompanying claims.

It is claimed:

1. A pump device for the peristaltic movement of fluid comprising:
    a rigid tube;
    a primary flexible tube connected to the rigid tube;
    a collection receptacle connected to the primary flexible tube;
    a peristaltic pump configured to apply peristaltic motion to the primary flexible tube, wherein the primary flexible tube is inserted through the peristaltic pump such that operation of the peristaltic pump applies peristaltic motion to the primary flexible tube to move fluid from the rigid tube, through the primary flexible tube, and then into the collection receptacle; and
    the peristaltic pump having an electrical circuit;
    wherein the primary flexible tube is restricted to being inserted through the peristaltic pump in one direction;
    wherein the primary flexible tube has a flexible tube connection and the peristaltic pump has a pump connection; and
    wherein on insertion of the primary flexible tube in said one direction, said flexible tube connection cooperates with said pump connection so as to complete a circuit connection in said electrical circuit and turn the peristaltic pump power on.

2. The pump device in claim 1 further comprising a connector, wherein the connector has one opening for inflow and a plurality of openings for outflow.

3. The pump device in claim 2, wherein the connector having one opening for inflow of fluid and a plurality of openings for outflow of fluid is a Y-connector.

4. The pump device in claim 1 further comprising an aspirator arranged for insertion into the body of a patient for communication with a collection of fluid within the body of the patient; the aspirator connected to the rigid tube; and wherein operation of the peristaltic pump applies peristaltic motion to the primary flexible tube to move fluid from the aspirator, through the rigid tube, through the primary flexible tube, and then into the collection receptacle.

5. The pump device in claim 4, wherein the aspirator is at least one of a sheath needle and a catheter.

6. The pump device in claim 1 further comprising a plurality of collection receptacles.

7. The pump device in claim 6, wherein the collection receptacles include at least one of a drainage bag and a syringe.

8. The pump device in claim 1 further comprising a plurality of at least one of clamps and valves.

9. The pump device in claim 8, further comprising a one way valve.

10. The pump device in claim 1, further comprising a fluid movement sensor.

11. A tube device for the peristaltic movement and collection of fluid comprising:
    an aspirator, wherein the aspirator is at least one of a sheath needle and a catheter;
    a rigid tube connected to the aspirator;
    a primary flexible tube connected to the rigid tube, wherein the primary flexible tube is configured for insertion in a peristaltic pump configured to apply peristaltic motion to the primary flexible tube such that operation of the peristaltic pump applies peristaltic motion to the primary flexible tube to move fluid from the aspirator, through the rigid tube, through the primary flexible tube, and then into a collection receptacle connected to the primary flexible tube;
    wherein the primary flexible tube has a first connector that cooperates with a second connector of the peristaltic pump when the primary flexible tube is inserted through the peristaltic pump so as to make a circuit connection of an electrical circuit of the peristaltic pump and turn the peristaltic pump power on.

12. The tube device of claim 11 further comprising a third connector, wherein the third connector has one opening for inflow of fluid and a plurality of openings for outflow of fluid.

13. The tube device of claim 12 further comprising a plurality of secondary flexible tubes, wherein the primary flexible tube is connected to the rigid tube and the inflow opening of the third connector and two or more secondary flexible tubes are connected to the outflow openings of the third connector.

14. The tube device of claim 13 further comprising a plurality of at least one of clamps and valves for placement on at least one of the primary flexible tube and the plurality of secondary flexible tubes.

15. The tube device of claim 11, wherein the collection receptacle is at least one of a drainage bag and a syringe.

16. A system for the peristaltic movement of fluid, comprising:
    an aspirator including at least one of a sheath needle and a catheter;
    a rigid tube fluidly connected to the aspirator;
    a primary flexible tube fluidly connected to the rigid tube;
    a peristaltic pump configured to apply peristaltic motion to the primary flexible tube, wherein the primary flexible tube is inserted through the peristaltic pump such that operation of the peristaltic pump applies peristaltic motion to the primary flexible tube;
    the peristaltic pump having an electrical circuit;
    a drainage bag fluidly connected to the primary flexible tube; and
    wherein the peristaltic pump is operable to move fluid from the aspirator, through the rigid tube, through the primary flexible tube, and then into the drainage bag;
    wherein primary flexible tube has a first connector and the peristaltic pump has a second connector;
    wherein on insertion of the primary flexible tube through said peristaltic pump, said first connector cooperates with said second connector and completes a circuit connection in said electrical circuit to turn the peristaltic pump power on; and wherein the rigid tube, the primary flexible tube and the drainage bag define a first collection flow path for the fluid, and wherein the system defines a second collection flow path for the fluid, the second collection flow path coupled to the first collection flow path.

17. The system of claim 16, also comprising a directional coupling mechanism that restricts insertion of the primary flexible tube through the peristaltic pump to only one direction.

18. The system of claim 16, wherein the sheath needle or the catheter is adapted to access fluid located within the abdomen or chest cavity of a patient.

19. The system of claim 18, wherein the aspirator includes the sheath needle.

20. The system of claim 18, wherein the rigid tube, the primary flexible tube and the drainage bag define a first collection flow path for the fluid, and wherein the system defines a second collection flow path for the fluid, the second collection flow path coupled to the first collection flow path.

21. A system for the peristaltic movement of fluid, comprising:
an aspirator arranged for insertion into the body of a patient for communication with a collection of fluid within the body of the patient;
a rigid tube connected to the aspirator;
a primary flexible tube having a first end and a second end, the first end being connected to the rigid tube;
a peristaltic pump configured to apply peristaltic motion to the primary flexible tube, wherein the primary flexible tube is restricted to being inserted through the peristaltic pump in one direction by a directional coupling mechanism such that operation of the peristaltic pump applies peristaltic motion to the primary flexible tube to move fluid from the aspirator, through the rigid tube, through the primary flexible tube, and out the second end of the primary flexible tube; and
the peristaltic pump having an electrical circuit;
wherein the primary flexible tube has a flexible tube connection and the peristaltic pump has a pump connection;
wherein insertion of the primary flexible tube in said one direction connects the flexible tube connection of the primary flexible tube with the pump connection of the peristaltic pump to complete a circuit connection in said electrical circuit and turn the peristaltic pump power on.

22. The system of claim 21, further comprising a one way valve to restrict the fluid flow to one direction.

23. The system of claim 21, further comprising a connector for connecting a syringe between the collection of fluid and a collection bag.

* * * * *